United States Patent
Bogan, Jr. et al.

(10) Patent No.: US 7,754,916 B2
(45) Date of Patent: Jul. 13, 2010

(54) PROCESS FOR CONVERTING A HYDROXYCARBOXYLIC ACID, OR SALTS THEREOF, TO AN UNSATURATED CARBOXYLIC ACID AND/OR ITS ESTERS

(75) Inventors: Leonard Edward Bogan, Jr., Lansdale, PA (US); Mark Anthony Silvano, New Hope, PA (US); Donald L. Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 12/283,050

(22) Filed: Sep. 9, 2008

(65) Prior Publication Data

US 2009/0076297 A1 Mar. 19, 2009

Related U.S. Application Data

(60) Provisional application No. 60/994,067, filed on Sep. 17, 2007.

(51) Int. Cl.
C07B 35/06 (2006.01)
(52) U.S. Cl. ...................................... 562/599
(58) Field of Classification Search ........................ None
See application file for complete search history.

(56) References Cited

U.S. PATENT DOCUMENTS

| | | | |
|---|---|---|---|
| 2,469,701 A | 5/1949 | Redmon et al. | |
| 2,859,240 A * | 11/1958 | Holmen | 560/212 |
| 4,282,323 A | 8/1981 | Yates | |
| 5,071,754 A * | 12/1991 | Walkup et al. | 435/135 |
| 6,187,951 B1 | 2/2001 | Baniel et al. | |
| 6,472,559 B2 | 10/2002 | Baniel et al. | |
| 6,897,338 B2 | 5/2005 | Zhong et al. | |
| 7,019,170 B2 | 3/2006 | Eyal et al. | |
| 7,186,856 B2 | 3/2007 | Meng et al. | |
| 2005/0221457 A1 | 10/2005 | Tsobanakis et al. | |
| 2005/0222458 A1 | 10/2005 | Cracium et al. | |

FOREIGN PATENT DOCUMENTS

| | | |
|---|---|---|
| EP | 0 181 718 A | 5/1986 |
| WO | WO 98/15518 A | 4/1998 |

* cited by examiner

*Primary Examiner*—Paul A Zucker
(74) *Attorney, Agent, or Firm*—Marcella M. Bodner

(57) ABSTRACT

A process for converting a salt of a hydroxycarboxylic acid to an unsaturated carboxylic acid, or esters thereof. The process involves converting an ammonium salt of a hydroxycarboxylic acid in aqueous solution to a corresponding hydroxycarboxylic acid and ammonium cation in aqueous solution; and separating the ammonium cation from the aqueous solution, leaving the hydroxycarboxylic acid in aqueous solution. The converting and separating steps may be accomplished by employing a hydrophobic acid or an acid ion exchange resin, each of which must have an acid dissociation constant, i.e., $pK_a$, at least 0.5 less that that of the salt of the hydroxycarboxylic acid. Where a hydrophobic acid is used, it must be immiscible in water, and its salt must also be immiscible in water, and the resulting multi-phase solution comprises an aqueous phase comprising the corresponding hydroxycarboxylic acid, as well as a non-aqueous phase comprising a neutralized acid. Alternatively, where the ion exchange resin is used, the aqueous solution of the ammonium salt of a hydroxycarboxylic acid is contacted with the resin, thereby converting the salt to a hydroxycarboxylic acid and capturing the ammonium cations on the resin. In either case, the aqueous solution is treated, such as by heating, to separate and recover the hydroxycarboxylic acid. The non-aqueous phase or resin is treated to separate and recover ammonia useful for preparing additional ammonium salt of a hydroxycarboxylic acid.

10 Claims, No Drawings

PROCESS FOR CONVERTING A HYDROXYCARBOXYLIC ACID, OR SALTS THEREOF, TO AN UNSATURATED CARBOXYLIC ACID AND/OR ITS ESTERS

This invention claims priority to U.S. Provisional Application No. 60/994,067 filed Sep. 17, 2007.

FIELD OF THE INVENTION

The present invention relates to a process for preparing an unsaturated carboxylic acid or its ester from the ammonium salt of a hydroxycarboxylic acid.

BACKGROUND OF THE INVENTION

Acrylic acid is currently made commercially by the two-step oxidation of propylene. More recent, but not-yet-commercial, technology exists for manufacture of acrylic acid by oxidation of propane. Propylene is a petroleum derivative, and its price reflects the growing scarcity and rising price of oil. Propane, derived from oil or natural gas liquids, makes a convenient fuel and is generally cheaper than propylene, however, its price has risen as its use as a substitute for petroleum fuels in energy production has increased. Both propylene and propane are non-renewable resources.

It is desirable to find a renewable feedstock material, such as biomass, from which acrylic acid may be economically manufactured on a commercial scale. Although no direct route from biomass to acrylic acid exists, 3-hydroxypropionic acid (i.e., beta-hydroxypropionic acid or 3HP), which is a hydroxycarboxylic acid and is prepared by fermentation of sugar(s), has the potential to be such a renewable feedstock material. Although lactic acid (2-hydroxypropionic acid) is a natural product and more readily available, it is difficult to dehydrate it to acrylic acid in good yield because of competing decarbonylation and decarboxylation reactions which occur simultaneously with dehydration. On the other hand, the dehydration of 3-hydroxycarboxylic acids is accomplished relatively easily. 3-hydroxypropionic acid is not yet commercially available, but bioengineers are working to develop bacteria and yeast that are capable of converting carbohydrates to 3HP in consistent high yields. Due to the sensitivity of such bacteria and yeast to pH levels, such fermentation processes are likely to produce a salt of 3HP, for example, the ammonium salt of 3HP, in aqueous solution.

U.S. Pat. No. 2,469,701 (Redmon) teaches a method for the preparation of acrylic acid (AA) by heating 3-hydroxypropionic acid (3HP) to a temperature between 130° C. and 190° C., in the presence of a dehydration catalyst, such as sulfuric acid or phosphoric acid, under reduced pressure. The best yields of AA from this process are reported to be about 86.4%, based on assumed 100% 3HP, and 77.4% based on ethylene cyanohydrin. However, no mention is made of converting salts of 3HP to AA, and, therefore, nor is there any discussion or guidance concerning recovery and recycle of the salt-forming neutralizing agent to form additional quantities of the salt of 3HP.

U.S. Patent Application Publication No. 2005/0222458 A1 (Craciun, et. al.) provides a process for the preparation of AA by heating 3HP or its derivatives obtained from microbial or plant cells. Examples are provided which demonstrate vapor-phase dehydration of 3HP in the presence of dehydration catalysts, such as packed beds of silica, alumina, or titania, and provide high yields (80.6% to 98.2%) of AA. No disclosure or suggestion, however, is made in this published application of using salts of 3HP as the initial feed material, nor how one would recapture, and reuse a salt-forming neutralizing agent to form more of the salt of 3HP.

U.S. Patent Application Publication No. 2005/0221457 A1 (Tsobanakis, et. al.) discloses a process for preparing a salt (or ester) of acrylic acid by heating the salt (or ester) of 3HP. However, the examples of this process provided concern only the conversion of sodium and calcium salts of 3HP at elevated pressure, and they achieve poor yields (41.8 and 48.7%) of AA. Furthermore, no description or guidance is provided concerning separation and recovery of a salt capable of forming the salt of 3HP used as the initial feed material.

U.S. Pat. No. 7,186,856 (Meng, et. al.) teaches a process for producing AA from the ammonium salt of 3HP, which involves a first step of heating the ammonium salt of 3HP in the presence of an organic amine or solvent that is immiscible with water, to form a two-phase solution and split the 3HP salt into its respective ionic constituents under conditions which transfer 3HP from the aqueous phase to the organic phase of the solution, leaving ammonia and ammonium cations in the aqueous phase. The organic phase is then back-extracted to separate the 3HP, followed by a second step of heating the 3HP-containing solution in the presence of a dehydration catalyst to produce AA. Thus, the process described in this published application cracks and frees the 3HP from the aqueous phase, permitting extraction of the 3HP into the organic phase, while leaving the ammonia behind in the aqueous phase. Although the examples provided in this published application allege AA yields from 32 to 90%, applicants were unable to reproduce these results when the 3HP solution was prepared from splitting the ammonium salt of 3HP, instead of using free 3HP. Furthermore, even if the claimed yields were obtainable, this process is undesirable because the salt-splitting step adds cost to the overall process by requiring additional materials, unit operations, and equipment, as well as by generating additional waste.

In view of the foregoing existing technologies, a process for efficiently converting ammonium salts of hydroxycarboxylic acids to unsaturated carboxylic acids, such as AA, on a commercial scale is still needed. The objective of the invention is to provide an economical process for converting the ammonium salts of hydroxycarboxylic acids to corresponding unsaturated carboxylic acids, such as AA A further objective is to provide a process which includes a method for recycling the ammonia derived from acidifying the ammonium salt of hydroxycarboxylic acid.

SUMMARY OF THE INVENTION

The present invention provides a process for preparing an unsaturated carboxylic acid, and esters thereof, from an ammonium salt of a hydroxycarboxylic acid wherein the process comprises the steps of: a) providing an aqueous solution comprising the ammonium salt of a hydroxycarboxylic acid; b) converting the ammonium salt of a hydroxycarboxylic acid to a corresponding hydroxycarboxylic acid and ammonium cation in aqueous solution; c) separating the ammonium cation from the aqueous solution, leaving the hydroxycarboxylic acid in aqueous solution.

The hydroxycarboxylic acid may be an α-hydroxycarboxylic acid, a β-hydroxycarboxylic acid, or an α-β-dihydroxycarboxylic acid. For example, without limitation, the hydroxycarboxylic acid may be any of: lactic acid, citric acid, 3-hydroxypropionic acid, 3-hydroxy-2-methylpropionic acid, 3-hydroxybutanoic acid, 3-hydroxy-2-methylbutanoic acid, 3-hydroxy-2-methylpentanoic acid, 3-hydroxy-3-methylbutanoic acid, 2,3-dimethyl-3-hydroxybutanoic acid, 3-hydroxy-3-phenylpropionic acid, and combinations thereof. For example, in one embodiment, the hydroxycarboxylic acid may be a beta-hydroxycarboxylic acid comprising beta-hydroxypropionic acid.

The unsaturated carboxylic acid, and esters thereof may be, for example, without limitation, acrylic acid, methacrylic acid, and esters thereof.

In accordance with the process of the present invention, the above-stated converting b) and separating c) steps are accomplished by one of the following techniques:

(1) adding a solution comprising a hydrophobic acid and, optionally, an organic solvent, to the aqueous solution, wherein the hydrophobic acid comprises a proton and a conjugate base, is immiscible in water, is capable of forming an ammonium salt which is also immiscible in water, and has an acid dissociation constant ($pK_a$) which is at least 0.5 less than the acid dissociation constant of the hydroxycarboxylic acid, to form a multi-phase solution which comprises an aqueous phase comprising the hydroxycarboxylic acid, which comprises the carboxylic anion and the proton, and a non-aqueous phase comprising a neutralized acid, which comprises the ammonium cation and the conjugate base, or (2) contacting the aqueous solution comprising the ammonium salt of a hydroxycarboxylic acid with an acid ion exchange resin having an acid dissociation constant ($pK_a$) which is at least 0.5 less than the acid dissociation constant of the hydroxycarboxylic acid, to form an aqueous solution comprising the corresponding hydroxycarboxylic acid and a non-aqueous ammonium cation-containing exchange resin.

The process of the present invention may comprise the step of: further treating the hydroxycarboxylic acid by a process selected from the group consisting of: dehydration to form the desired unsaturated carboxylic acid product and esterification to form the desired ester of unsaturated carboxylic acid product. Either or both of dehydration and esterification may occur in the presence of a suitable catalyst. The process of the present invention may further comprise the step of separating the unsaturated carboxylic acid (or esters thereof) product from the aqueous solution.

The process of the present invention may comprise the steps of: (d) further treating the ammonium cations to form and separate ammonia; (e) and recovering and recycling the ammonia to an upstream process step in which quantities of an ammonium salt of a hydroxycarboxylic acid are formed in an aqueous solution of a hydroxycarboxylic acid.

In an embodiment where technique (1) has been applied the neutralized acid, comprising the ammonium cation and the conjugate base of the hydrophobic acid, is treated by heating to form and separate ammonia from the non-aqueous phase, and then the ammonia is recovered and recycled to another process step in which quantities of an ammonium salt of a hydroxycarboxylic acid are formed in aqueous solution.

In an embodiment where technique (2) has been applied to form a cation-containing ion exchange resin which comprises the ammonium cations, the ammonium cations are treated by: washing the ammonium cation-containing ion exchange resin with a washing acid, having a proton and a conjugate base and having an acid dissociation constant ($pK_a$) which is at least 0.5 less than the acid dissociation constant of the resin, to separate and recover an ammonium salt, comprising the ammonium cation and the conjugate base of the washing acid; heating the ammonium salt to regenerate ammonia and the washing acid; recycling the ammonia to an upstream process step in which quantities of an ammonium salt of a hydroxycarboxylic acid are produced; and recycling the washing acid for washing the additional quantities of ammonia-containing resin and recovering the ammonia.

DETAILED DESCRIPTION OF THE INVENTION

The present invention provides a process for preparing an unsaturated carboxylic acid, and esters thereof, from an ammonium salt of a hydroxycarboxylic acid. The unsaturated carboxylic acid and esters thereof may, for example, without limitation, be acrylic acid, methacrylic acid, crotonoic acid, or esters thereof.

The hydroxycarboxylic acid may be, for example, an α-hydroxycarboxylic acid, a β-hydroxycarboxylic acid, or an α,β-dihydroxycarboxylic acid selected from the group consisting of: lactic acid, citric acid, 3-hydroxypropionic acid, 3-hydroxy-2-methylpropionic acid, 3-hydroxybutanoic acid, 3-hydroxy-2-methylbutanoic acid, 3-hydroxy-2-methylpentanoic acid, 3-hydroxy-3-methylbutanoic acid, 2,3-dimethyl-3-hydroxybutanoic acid, 3-hydroxy-3-phenylpropionic acid, and combinations thereof. For example, the ammonium salt of a hydroxycarboxylic acid may be the ammonium salt of lactic acid, or even the ammonium salt of 3-hydroxypropionic acid. An aqueous solution comprising the ammonium salt of a hydroxycarboxylic acid may, for example, comprise at least 0.1% by weight of the ammonium salt of the hydroxycarboxylic acid, based on the total weight of the aqueous solution and salt of the hydroxycarboxylic acid.

In aqueous solution, the dissociation of a hydroxycarboxylic acid is characterized by an acid dissociation constant. As used herein, and as is well known to persons of ordinary skill, the term "acid dissociation constant," or "$pK_a$," is related to the equilibrium constant for the dissociation of an acid in aqueous solution into its consituent cation (often a proton), and anion. The acid dissociation constant, $pK_a$, may also be referred to as the acidity constant, or the acid-ionization constant. Determination of the acid dissociation constant for many, many acids has already been accomplished in the past and this information may be found easily in reference materials generally available to persons of ordinary skill in the relevant art. For example, acid dissociation constants for many acids are available from the CRC Handbook of Chemistry and Physics, CRC Press, Boca Raton, Fla.

The process of the present invention involves converting the ammonium salt of a hydroxycarboxylic acid to a corresponding hydroxycarboxylic acid and ammonium cations in aqueous solution, and separating the ammonium cation from the aqueous solution, and leaving behind the hydroxycarboxylic acid in aqueous solution, thereby avoiding the need to back extract the hydroxycarboxylic acid from an aqueous phase solution.

In addition, once the ammonium cations have been separated from the aqueous phase into a non-aqueous carrier, they may be treated to reform and recover ammonia. Thus, the present invention may further comprise treating the ammonium cations to form and separate ammonia from whatever carrier is holding the ammonium cations, for example, an organic solvent or a cation exchange resin, as will be described in further detail hereinafter. The separated ammonia may then be recovered and recycled to produce more ammonium salt of a hydroxycarboxylic acid in aqueous solution in one or more upstream processes.

The aforesaid converting and separating steps, wherein the hydroxycarboxylic acid remains in aqueous solution and the ammonium cations are removed from the aqueous solution and into a non-aqueous carrier, may be accomplished, in accordance with the present invention, using the following techniques.

In one embodiment of the present invention, a hydrophobic acid is added to the aqueous solution. The hydrophobic acid may be in solution with an organic solvent, such as a xylene, or heptane, however, this not necessary. The hydrophobic acid comprises a proton and a conjugate base, and has the following characteristics: it is (1) immiscible in water, (2) capable of forming an ammonium salt which is also immiscible in water, and (3) has an acid dissociation constant ($pK_a$) which is at least 0.5 less than the acid dissociation constant of the hydroxycarboxylic acid. For example, the $pK_a$ of 3-hydroxypropionic acid is about 4.5, so the acid would have to be an acid that has a $pK_a$ of 4.0 or less (4.5-0.5). As another example, the hydrophobic acid may have an acid dissociation constant ($pK_a$) which is at least 1.0 less, or even 2.0 less, than the acid dissociation constant of the hydroxycarboxylic acid. The optional solvent, when present, should also be immiscible in water. Upon addition of the hydrophobic acid, or immiscible acid-solvent solution, to the aqueous solution comprising the ammonium salt of a hydroxycarboxylic acid, a multi-phase solution forms and comprises an aqueous phase comprising the hydroxycarboxylic acid (which comprises the carboxylic anion and the proton), and a non-aqueous phase comprising a neutralized acid (which comprises the ammonium cation and the conjugate base of the hydrophobic acid), and the organic solvent, if present.

When the foregoing technique is applied to form the multi-phase solution, in which the non-aqueous phase comprises a neutralized acid which comprises ammonium cations and the conjugate base of the hydrophobic acid and, optionally, an organic solvent, the ammonium cations are treated by heating the non-aqueous phase to form and separate ammonia therefrom. The ammonia may then be easily recovered and recycled by known conventional means for use in producing more aqueous solution of an ammonium salt of a hydroxycarboxylic acid, such as, for example, in an upstream process in which quantities of an ammonium salt of a hydroxycarboxylic acid are formed in aqueous solution from a fermentation broth.

In another embodiment of the present invention, the aqueous solution comprising the ammonium salt of a hydroxycarboxylic acid is contacted with an acid ion exchange resin having an acid dissociation constant ($pK_a$) which is at least 0.5 less than the acid dissociation constant of the hydroxycarboxylic acid. For example, the $pK_a$ of 3-hydroxypropionic acid is about 4.5, so the ion exchange resin would have to have a $pK_a$ of 4.0 or less (4.5-0.5). It is noted, for example, that the resin may have an acid dissociation constant ($pK_a$) which is at least 1.0 less, or even 2.0 less, than the acid dissociation constant of the hydroxycarboxylic acid. Suitable resins are commercially available from a number of sources, including but not limited to, NAFION™ resins available from E.I. DuPont de Nemours and Co. of Wilmington, Del., USA, AMBERLYST® resins available from Rohm and Haas Company of Philadelphia, Pa., USA, and DOWEX™ resins from Dow Chemical of Midland, Mich., USA. This contact of the aqueous solution with the acid ion exchange resin produces an aqueous solution comprising the corresponding hydroxycarboxylic acid and an ammonium cation-containing ion exchange resin. Contacting the aqueous solution with the acid ion exchange resin may be accomplished in any way known to persons skilled in the art such as, for example, in a column, under suitable conditions well within the ability of ordinarily skilled persons to determine.

The ammonium cations are further treated by washing the ammonium cation-containing ion exchange resin with a washing acid to separate and recover an ammonium salt, comprising the ammonium cation and the conjugate base of the washing acid. The washing acid has a proton and a conjugate base, as well as an acid dissociation constant ($pK_a$) which is at least 0.5 less than the acid dissociation constant of the acid ion exchange resin. Heating the resulting washing acid solution, which now comprises the ammonium cations, will regenerate ammonia and the strong acid. Again, the ammonia may be easily recovered and recycled for use in producing more aqueous solution of an ammonium salt of a hydroxycarboxylic acid, such as, for example, in an upstream process in which quantities of an ammonium salt of a hydroxycarboxylic acid are formed in aqueous solution from a fermentation broth. Also, the regenerated washing acid may be recovered and recycled for washing ammonia-containing ion exchange resin and recovering the ammonia.

Regardless of the technique employed to convert the ammonium salt of a hydroxycarboxylic acid to its corresponding hydroxycarboxylic acid in aqueous solution and separate ammonium cations from the aqueous solution, into a carrier, such as for example, an organic solvent or a cation exchange resin, the aqueous solution may be separated from the carrier to facilitate further processing of both the hydroxycarboxylic acid and the ammonium cations.

Additionally, the hydroxycarboxylic acid may be further treated by a process selected from the group consisting of: dehydration to form the desired unsaturated carboxylic acid product and esterification to form the desired ester of an unsaturated carboxylic acid product. The dehydration may be performed in the presence of a dehydration catalyst, such as; for example, sulfuric acid, or phosphoric acid. The reaction temperature suitable for dehydration of hydroxycarboxylic acid will depend to some degree on which hydroxycarboxylic acid is being dehydrated, whether the process occurs in the vapor or liquid phase, as well as whether and what type of catalyst is used. It is within the ability of persons of ordinary skill to select suitable dehydration temperatures, which are typically between 100° C. and 400° C., such between 100° C. and 350° C., or even 175° C. to 325° C. Similarly, the esterification may be performed in the presence of an esterification catalyst, such as, for example, sulfuric acid, or para-toluenesulfonic acid or methanesulfonic acid. The reaction temperature suitable for esterification will depend to some degree on which hydroxycarboxylic acid is used, as well as whether and what type of catalyst is used. It is within the ability of persons of ordinary skill to select suitable esterification temperatures, which are typically between 100° C. and 300° C., such between 100° C. and 250° C., or even 125° C. to 225° C. As will be readily recognized by persons of ordinary skill in the art, dehydration of the hydroxycarboxylic acid, followed by esterification, may be efficiently and advantageously accomplished to form the desired ester of an unsaturated carboxylic acid product. Where dehydration and esterification are performed concurrently, typical reaction temperatures are between 100° C. and 300° C., such between 100° C. and 250° C., or even 125° C. to 225° C. and are easily determinable by persons of ordinary skill.

It is noted that prior processes, such as those described in U.S. Pat. No. 7,186,856, transfer hydroxypropionate anions (i.e., the carboxylic anion) from an initial aqueous solution containing A3HP, into a non-aqueous (organic) solution which will require further processing or treatment (e.g., back extraction) to form an aqueous solution of 3HP for dehydration and/or esterification. Furthermore, these known processes leave behind an aqueous solution comprising ammonia, ammonium cations and protons.

The process of the present invention, on the other hand, transfers ammonia, from the initial aqueous solution comprising the ammonium salt of a hydroxycarboxylic acid, into a non-aqueous carrier (such as a hydrophobic acid, with or without an organic solvent, or an acid ion exchange resin), leaving the hydroxycarboxylic acid (e.g., 3HP) behind in the aqueous solution, which can then be subjected to dehydration and/or esterification leading to increased overall yield of AA or its esters compared to previously employed processes. The unsaturated carboxylic acid (e.g., AA) may be separated from the aqueous phase by known conventional means such as, without limitation, distillation or melt crystallization. The process of the present invention further facilitates reconstitution and recycle of ammonia, which is still present in the non-aqueous carrier (i.e., hydrophobic acid with or without organic solution, or ion exchange resin). For example, the reconstituted and recovered ammonia may be recycled and used to form additional ammonium salt of 3HP from a raw fermentation product. The process of the present invention further facilitates, after reconstituting and recovering the ammonia, reconstitution and separation of the original hydrophobic acid or acid ion exchange resin, which can also then be recycled and re-used.

The present invention will now be described in greater detail in connection with an embodiment in which the salt of a hydroxycarboxylic acid is the ammonium salt of 3-hydroxypropionic acid (A3HP), which is converted to acrylic acid using the process of the present invention, in particular, the embodiment which employs a hydrophobic acid. As will be recognized by persons of ordinary skill in the relevant art, the process of the present invention is equally applicable to conversion of other salts of 3HP, besides the ammonium salt, to produce carboxylic acids other than, or in addition to, acrylic acid.

An acid having a $pK_a$ at least 0.5 less that than that of the 3HP, which means lower than about 4.0 is introduced into the solution of A3HP, then the ammonium ion will be displaced from the 3HP anion and replaced by a proton, yielding 3HP and a neutralized acid comprising the ammonium salt of the conjugate base of the other acid. The ammonium salt may be extracted into the non-aqueous phase, while 3HP remains in the aqueous phase. This extraction step could, for example be suitably effected in a countercurrent extractor. The aqueous 3HP can then be either distilled directly (for subsequent dehydration to AA), or else dehydrated to AA by heating the solution, in the presence of a catalyst or not, and then separating the AA product, for example, by distillation.

For example, where the added acid-solvent solution was dinonylnaphthalenesulfonic acid ($pK_a$=about −1.7), dissolved in heptanes to make it liquid, then the organic phase would contain the ammonium salt of dinonylnaphthalenesulfonic acid and heptanes, and the aqueous phase would contain 3HP. The phases could be separated, and aqueous 3HP converted to AA by known methods (we have observed 99% yield using a modified procedure in our lab). The organic phase could be heated to liberate ammonia and regenerate the dinonylnaphthalenesulfonic acid.

Thus, with the proper choice of added acid, the ammonia will remain undistilled in solution as the ammonium salt of the conjugate base of the added acid. Upon further heating, ammonia can be released from this salt so that both the ammonia and the acid can be recycled.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

EXAMPLES

Formation of an Aqueous Solution Comprising a Salt of 3HP

The ammonium salt of 3HP was prepared from a 30% aqueous solution of sodium-3-hydroxypropionate and dimers by ion-exchange on a column of Amberlite® IR-120 resin in the ammonium form. The salt solution was sampled for NMR analysis and analyzed for sodium and ammonium ion content by ion chromatography.

Example 1

Part A

Extraction of Ammonium 3HP with a Strong Acid, Immiscible in Water

Aqueous ammonium 3-hydroxypropionate solution (40 g, 28% A3HP, 104.6 mmol) was extracted with 100 g dinonyl naphthalene sulfonic acid solution in heptane (approximate $pKa$=−1.7) (Nacure 1052, commercially available from King Industries of Norwalk, Conn., USA). After separating about 20 ml of aqueous solution, the organic phase was shaken with an additional 110 ml n-heptane and 10 ml water. 10 ml of aqueous phase separated, and was removed. The organic phase was shaken with another 20 ml water, and 20 ml aqueous phase was removed. The organic phase was shaken with another 20 ml water, and 20 ml aqueous phase was removed. Total removed: 69.0 g, 0.90% water by Karl-Fischer titration (yield 6.9 g, 3-hydroxypropionic acid, 70 mmol).

Example 1

Part B

Dehydration of 3HP with Dehydration Catalyst (Sulfuric Acid)

The above-described 3HP product was dehydrated using 96% sulfuric acid as catalyst (45 g sulfuric acid heel charge, 160° C., 100 mm Hg, sample feed rate 8 ml/hr, catalyst feed rate 0.6 ml/hr, bleed rate 1.1 g/hr) to give an AA yield of 96.2% (carbon balance accountability was 97.0%).

Example 2

Extraction of Ammonium 3HP with an Acid Ion Exchange Resin

Aqueous ammonium 3-hydroxypropionate solution (40 g, 28% A3HP, 104.6 mmol) is diluted with water to 105 ml, and the resulting solution passed through a bed of 1 kg Amberlite® IR-120 resin in the acid form at a rate of 4 bed volumes/hr. The column is then washed with 4 bed volumes of water. Water is removed from the combined eluant to make a 30% w/w aqueous solution of 3-hydroxypropionic acid (3HP).

This material is dehydrated using 96% sulfuric acid as catalyst (45 g sulfuric acid heel charge, 160° C., 100 mm Hg, sample feed rate 8 ml/hr, catalyst feed rate 0.6 ml/hr, bleed rate 1.1 g/hr) to give acrylic acid.

What is claimed is:

1. A process for preparing an unsaturated carboxylic acid, and esters thereof, from an ammonium salt of a beta-hydroxypropionic acid, said process comprising:

a) providing an aqueous solution comprising the ammonium salt of a beta-hydroxypropionic acid;

b) converting the ammonium salt of a beta-hydroxypropionic acid to a corresponding beta-hydroxypropionic acid and ammonium cation in aqueous solution; and c) separating the ammonium cation from the aqueous solution, leaving the beta-hydroxypropionic acid in aqueous solution;

wherein said converting and separating steps b) and c) are accomplished by a technique selected from the group consisting of:

(1) adding a solution comprising a hydrophobic acid and, optionally, an organic solvent, to the aqueous solution, wherein the hydrophobic acid comprises a proton and a conjugate base, is immiscible in water, is capable of forming an ammonium salt which is also immiscible in water, and has an acid dissociation constant ($pK_a$) which is at least 0.5 less than the acid dissociation constant of the beta-hydroxypropionic acid, to form a multi-phase solution which comprises an aqueous phase comprising the beta-hydroxypropionic acid, which comprises the carboxylic anion and the proton, and a non-aqueous phase comprising a neutralized acid, which comprises the ammonium cation and the conjugate base of the hydrophobic acid, and (2) contacting the aqueous solution comprising the ammonium salt of beta-hydroxypropionic acid with an acid ion exchange resin having an acid dissociation constant ($pK_a$) which is at least 0.5 less than the acid dissociation constant of the beta-hydroxypropionic acid, to form an aqueous solution comprising the corresponding beta-hydroxypropionic acid and a non-aqueous ammonium cation-containing exchange resin.

2. The process of claim 1, wherein said unsaturated carboxylic acid, and esters thereof is selected from the group consisting of: acrylic acid, methacrylic acid, and esters thereof.

3. The process of claim 1, further comprising the step of:

(d) further treating the beta-hydroxypropionic acid by a process selected from the group consisting of: dehydration to form the desired unsaturated carboxylic acid product and esterification to form the desired ester of an unsaturated carboxylic acid product.

4. The process of claim 3, wherein dehydration of said beta-hydroxypropionic acid occurs in the presence of a dehydration catalyst.

5. The process of claim 3, wherein the esterification of said beta-hydroxypropionic acid occurs in the presence of an esterification catalyst.

6. The process of claim 3, further comprising the step of separating the unsaturated carboxylic acid product from the aqueous solution.

7. The process of claim 1, further comprising the steps of: further treating the ammonium cations to form and separate ammonia; and recovering and recycling the ammonia to an upstream process step in which quantities of an ammonium salt of a beta-hydroxypropionic acid are formed in an aqueous solution of a beta-hydroxypropionic acid.

8. The process of claim 7, wherein technique (1) is applied to form the multi-phase solution which comprises a non-aqueous phase comprising a neutralized acid and, optionally, an organic solvent, and the neutralized acid comprises the ammonium cation and the conjugate base of the hydrophobic acid, and wherein the non-aqueous phase comprising the neutralized acid, is treated by heating to form and separate ammonia from the non-aqueous phase; and the ammonia is recovered and recycled to another process step in which additional quantities of an ammonium salt of a beta-hydroxypropionic acid are formed in aqueous solution.

9. The process of claim 7, wherein technique (2) is applied to form an aqueous solution comprising the corresponding beta-hydroxypropionic acid and a cation-containing ion exchange resin which comprises the ammonium cations, and the ammonium cations are treated by:

washing the ammonium cation-containing ion exchange resin with a washing acid, having an acid dissociation constant ($pK_a$) which is at least 0.5 less than the acid dissociation constant of the resin, to separate and recover an ammonium salt, comprising the ammonium cation and the conjugate base of the washing acid;

heating the ammonium salt to regenerate ammonia and the washing acid; recycling the ammonia to an upstream process step in which quantities of an ammonium salt of a beta-hydroxypropionic acid are produced; and recycling the washing acid for washing the additional quantities of ammonia-containing resin and recovering the ammonia.

10. The process of claim 1, wherein the aqueous solution comprises at least 0.1% by weight of the salt of a beta-hydroxypropionic acid, based on the total weight of the aqueous solution and salt of a beta-hydroxypropionic acid.

* * * * *